(12) United States Patent
Akiyama et al.

(10) Patent No.: US 6,218,675 B1
(45) Date of Patent: Apr. 17, 2001

(54) CHARGED PARTICLE BEAM IRRADIATION APPARATUS

(75) Inventors: Hiroshi Akiyama, Hitachi; Kazuo Hiramoto, Hitachiota; Koji Matsuda; Tetsuro Norimine, both of Hitachi, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/136,308

(22) Filed: Aug. 19, 1998

(30) Foreign Application Priority Data

Aug. 28, 1997 (JP) .................................................. 9-232114

(51) Int. Cl.⁷ ................................................... H01J 37/14
(52) U.S. Cl. .............................. 250/492.3; 250/396 ML; 250/397; 250/398
(58) Field of Search .................................... 250/492.3, 398, 250/396 ML, 492.21, 397

(56) References Cited

U.S. PATENT DOCUMENTS

| | | | | |
|---|---|---|---|---|
| 4,442,352 | * | 4/1984 | Brahme | 250/493.1 |
| 4,726,046 | * | 2/1988 | Nunan | 250/492.3 |
| 4,922,106 | * | 5/1990 | Berrian et al. | 250/398 |
| 5,267,294 | * | 11/1993 | Kuroda et al. | 250/492.3 |
| 5,751,002 | * | 5/1998 | Ogata et al. | 250/492.21 |
| 5,969,367 | * | 10/1999 | Hiramoto et al. | 250/492.3 |

* cited by examiner

*Primary Examiner*—Bruce C. Anderson
(74) *Attorney, Agent, or Firm*—Antonelli, Terry, Stout & Kraus LLP

(57) ABSTRACT

A charged particle beam irradiation apparatus for irradiating a target with a charged particle beam emitted from an accelerator includes a plurality of scanning electromagnets, and a quadrupole electromagnet is used between two of the plurality of the scanning electromagnets.

11 Claims, 5 Drawing Sheets

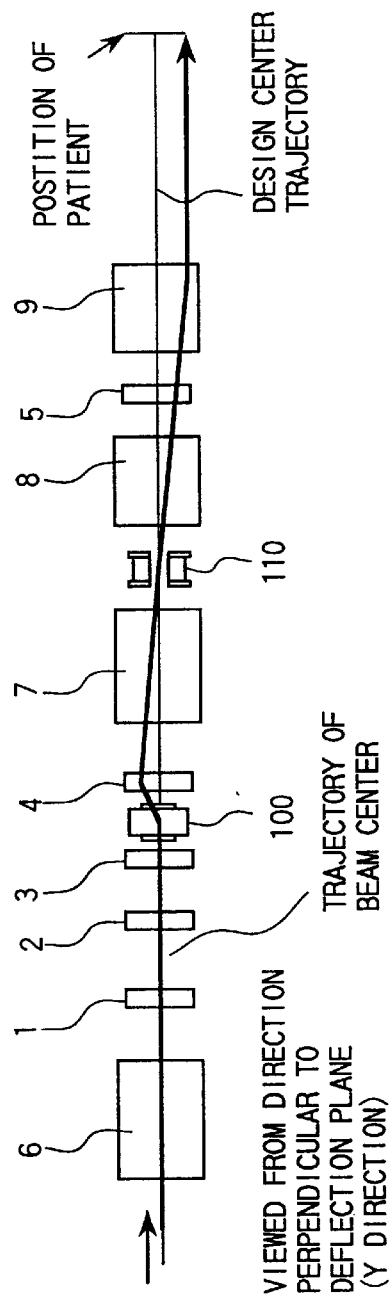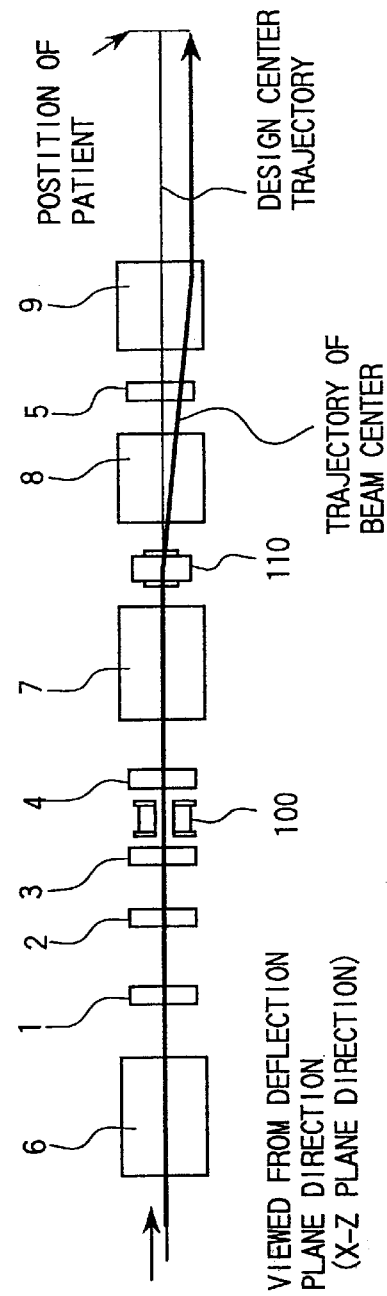

CHARGED PARTICLE BEAM IRRADIATION APPARATUS

BACKGROUND OF THE INVENTION

The present invention relates to a charged particle beam irradiation apparatus for irradiating a target object with a charged particle beam for medical treatment of cancer, bactericide in foods, improvement of plant breeding, non-destructive inspection of machines, and the invention relates especially to a charged particle beam irradiation apparatus which is capable of reducing power consumption.

In using a charged particle beam (hereafter, referred to simply as a beam) of high energy, which is generated by an accelerator, for medical treatment of cancer, etc., there is a method in which the diseased part is scanned with a charged particle beam, and another method in which the diameter of the charged particle beam is enlarged to make its dose distribution uniform and in which the enlarged charged particle beam is then shaped by using a collimator to fit to the shape of the target object, that is, the diseased part.

In the above two irradiation methods, the method of scanning a target with a charged particle beam has been implemented using the following methods: that is, the wobbler method of scanning a target with a charged particle beam, the raster scanning method of scanning a target with a charged particle beam in a zigzag manner, and the pixel scanning method of irradiating a target in a pixel state manner.

In the above scanning methods, two electromagnets are used, and the beam deflecting directions of the first and second electromagnets are set perpendicular to each other. Also, a plane perpendicular to the axial direction of the beam is scanned by the beam deflected by these electromagnets.

FIG. 7 is a schematic diagram of the composition of a conventional charged particle beam irradiation apparatus in which a beam irradiation unit using the wobbler method is installed in a rotation gantry. A charged particle beam emitted from an accelerator (not shown in the figure) is inputted into the rotation gantry and outputted from an irradiation nozzle 40. The diseased part is circularly scanned with the charged particle beam output from the irradiation nozzle 40 by two scanning electromagnets 100 and 110. The scanning electromagnet 100 deflects the beam in the X direction, and the scanning electromagnet 110 deflects the beam in the Y direction. By changing the amount of deflection of the beam in each scanning electromagnet with time, circular scanning can be performed.

In the above-mentioned conventional technique, it is necessary to set the gap between magnetic poles of the scanning electromagnet 110 wide enough so that the beam deflected by the scanning electromagnet 100 is prevented from striking the magnetic poles of the scanning electromagnet 110, since the deflection direction in the scanning electromagnet 100 is parallel to the magnetic poles of the scanning electromagnet 110. Widening the gap between the magnetic poles causes a problem in that a larger current is required in order to generate a magnetic field having the necessary strength, which increases the power consumption of the irradiation apparatus.

SUMMARY OF THE INVENTION

An object of the present invention is to provide a charged particle beam apparatus capable of reducing the power consumption of a scanning electromagnet by narrowing the gap between magnetic poles of the scanning electromagnet.

The first feature of the present invention to attain the above object is that, in a charged particle beam irradiation apparatus including a plurality of scanning electromagnets for irradiating a target with a charged particle beam emitted from an accelerator, a quadrupole electromagnetic used between two (the first and second ones) of the scanning electromagnets.

By providing a quadrupole electromagnet between two of the scanning electromagnets, it is possible to adjust betatron oscillation in the charged particle beam so that the crossing point of the trajectory of the beam center and the design center trajectory of the charged particle beam irradiation apparatus (the trajectory of the center on the beam axis when the beam is not deflected by any one of the scanning electromagnets, and hereafter, simply described as the design center trajectory) exists within an effective magnetic field range of the second scanning electromagnet. Thus, the interval between the magnetic poles in the second scanning electromagnet can be narrowed, which can reduce the power consumption of the second scanning electromagnet.

The second feature of the present invention to attain the above object is that the above mentioned charged particle beam irradiation apparatus includes a power source for feeding current to the quadrupole electromagnet and a control unit for controlling the current output from the power source, wherein the two scanning electromagnets comprise a first scanning electromagnet, and a second scanning electromagnet provided downstream of the first scanning electrode, the quadrupole electromagnet being sandwiched between the first and second scanning electromagnets, and a control unit which controls the current so that the crossing point of the trajectory of the beam center and the design center trajectory of the beam irradiation apparatus exists within an effective magnetic field range of the second scanning electromagnet.

By controlling the current fed to the quadrupole electromagnet provided between the two scanning electromagnets so that the crossing point of the trajectory of the beam center and the design center trajectory of the beam irradiation apparatus exists within an effective magnetic field range of the second scanning electromagnet, the interval of magnetic poles in the scanning electromagnet can be narrowed, which can reduce the power consumption of the second scanning electromagnet.

The third feature of the present invention to attain the above object is that, in the above mentioned charged particle beam irradiation apparatus, the crossing point of the trajectory of the beam center and the design center trajectory of the beam irradiation apparatus exists within an effective magnetic field range and is adjusted to be positioned at the center of the second scanning electromagnet.

By positioning the crossing point of the trajectory of the beam center and the design center trajectory of the beam irradiation apparatus within the effective magnetic field range at the center of the second scanning electromagnet, the interval between the magnetic poles in the scanning electromagnet can be minimally narrowed, which can largely reduce the power consumption of the second scanning electromagnet.

The fourth feature of the present invention to attain the above object is that the above mentioned charged particle beam irradiation apparatus includes a power source for feeding current to the quadrupole electromagnet and a control unit for controlling the current output from the power source, wherein the two scanning electromagnets comprise a first scanning electromagnet, and a second scanning electromagnet provided downstream of the first scanning electrode, the quadrupole electromagnet being sandwiched between the first and second scanning electromagnets, and a control unit which controls the current so that the difference between phases in betatron oscillation of the charged particle beam in the first and second scanning electromagnets is approximately an integer multiple of 180 deg.

By controlling the current so that the difference between phases in betatron oscillation of the charged particle beam in the first and second scanning electromagnets is approximately an integer multiple of 180 deg., since the crossing point of the trajectory of the beam center and the design center trajectory of the beam irradiation apparatus exists within an effective magnetic field range of the second scanning electromagnet, the interval between the magnetic poles in the scanning electromagnet can be narrowed, which can reduce the power consumption of the second scanning electromagnet.

The fifth feature of the present invention to attain the above object is that, in a charged particle beam irradiation apparatus including a plurality of scanning electromagnets for irradiating a target with a charged particle beam emitted from an accelerator, the plurality of the scanning electromagnets include a first scanning electromagnet and a second scanning electromagnet provided downstream of the first scanning electromagnet, and the crossing point of the trajectory of the beam center and the design center trajectory of the beam irradiation apparatus exists within an effective magnetic field range of the second scanning electromagnet.

Since the crossing point of the trajectory of the beam center and the design center trajectory of the beam irradiation apparatus exists within an effective magnetic field range of the second scanning electromagnet, the interval between the magnetic poles in the scanning electromagnet can be narrowed, which can reduce the power consumption of the second scanning electromagnet.

The sixth feature of the present invention to attain the above object is that, in a charged particle beam irradiation apparatus including a plurality of scanning electromagnets for irradiating a target with a charged particle beam emitted from an accelerator, the plurality of the scanning electromagnets include a first scanning electromagnet and a second scanning electromagnet provided downstream of the first scanning electromagnet, and the difference between phases in betatron oscillation of the charged particle beam in the first and second scanning electromagnets is approximately an integer multiple of 180 deg.

Since the difference between phases in betatron oscillation of the charged particle beam at the first and second scanning electromagnets is approximately an integer multiple of 180 deg., the crossing point of the trajectory of the beam center and a design center trajectory of the beam irradiation apparatus can be set within an effective magnetic field range of the second scanning electromagnet. Therefore, the interval between the magnetic poles in the scanning electromagnet can be narrowed, which can reduce the power consumption of the second scanning electromagnet.

The seventh feature of the present invention to attain the above object is that, in a charged particle beam irradiation apparatus including a plurality of scanning electromagnets, for irradiating a target with a charged particle beam emitted from an accelerator, at least one of a quadrupole electromagnet and a bending electromagnet is provided downstream of the scanning electromagnet existing furthest downstream among the plurality of the scanning electromagnets.

By providing at least one quadrupole electromagnet and a bending electromagnet downstream of the scanning electromagnet existing furthest downstream among the plurality of the scanning electromagnets, the trajectory of the center of the beam can be set parallel to the design center trajectory of the beam irradiation apparatus at the position of the target. Thus, it is possible to reduce the dose to the normal area surrounding the diseased part.

The eighth feature of the present invention to attain the above object is that the above charged particle beam irradiation apparatus including a plurality of scanning electromagnets also includes a bending electromagnet, power sources for feeding current to the quadrupole electromagnet and the bending electromagnet, and a control unit for controlling the current output from the power sources, wherein the control unit controls the current output from the power sources so that the trajectory of the center of the beam positioned on the target is parallel to the design center trajectory of the beam irradiation apparatus.

By controlling the current fed to the quadrupole electromagnet and the bending electromagnet so that the trajectory of the center of the beam positioned on the target is parallel to the design center trajectory of the beam irradiation apparatus, it is possible to reduce the dose to the normal surrounding are the diseased part.

The ninth feature of the present invention to attain the above object is that the above charged particle beam irradiation apparatus has a rotation gantry, wherein a plurality of the scanning electromagnets are arranged in a beam transport system of the rotation gantry.

By arranging a plurality of the scanning electromagnets in the beam transport system of the rotation gantry, it is possible to decrease the radius of rotation of the rotation gantry. Therefore, the size of the building containing the rotation gantry can be reduced, which can reduce the construction cost.

The tenth feature of the present invention to attain the above object is that, in the above charged particle beam irradiation apparatus, a beam scattering part is provided along the trajectory of the charged particle beam.

By providing the beam scattering part along the trajectory of the charged particle beam, it is possible to enlarge the diameter of the charged particle beam with beam scattering, which can reduce the amount of scanning operations. Thus, the irradiation time of the charged particle beam can be decreased.

BRIEF DESCRIPTION OF THE DRAWINGS

FIGS. 5A and 5B are schematic diagrams which show the center trajectory of the charged particle beam and the arrangement of electromagnets in the embodiment shown in FIG. 4.

DETAILED DESCRIPTION OF THE EMBODIMENTS

Hereinafter, embodiments of the present invention will be explained in detail with reference to the drawings.

Figure 1:
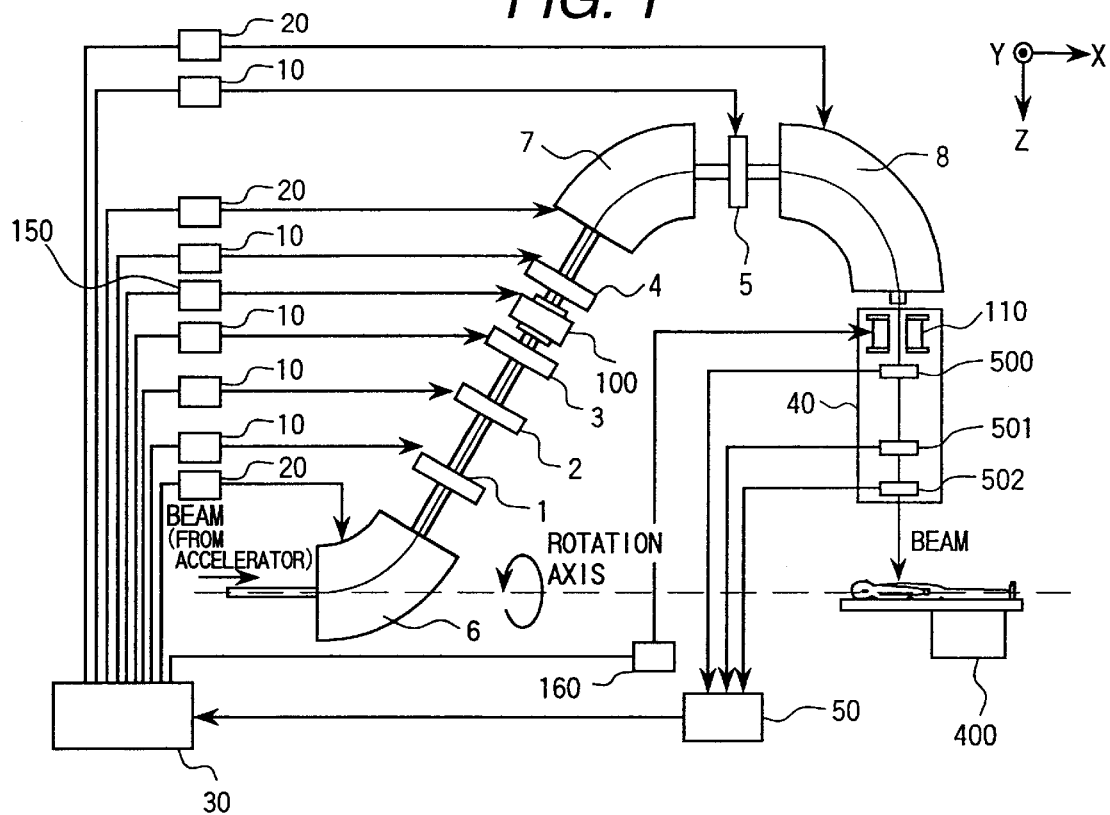
FIG. 1 is a schematic diagram showing the composition of a charged particle beam irradiation apparatus representing a first embodiment of the present invention.

Embodiment 1:

FIG. 1 shows a schematic diagram illustrating the composition of a charged particle beam irradiation apparatus representing an embodiment of the present invention. The beam irradiation apparatus of the present invention is used for medical treatment of a disease, for example, cancer, by irradiating the diseased part with a charged particle beam (hereafter, referred to as a beam), and the apparatus includes a rotation gantry capable of rotating around a bed 400 for a patient.

In FIG. 1, the beam emitted from an accelerator is inputted into the rotation gantry. The beam inputted into the rotation gantry is transported along a preset trajectory to an irradiation nozzle 40 by magnetic fields generated by quadrupole electromagnets 1–5 and bending electromagnets 6, 7, and 8. A power source 10 is provided for each of the quadrupole electromagnets 1–5, and each of the quadrupole electromagnets 1–5 generates a magnetic field whose strength corresponds to the value of current fed to it. Further, a power source 20 is provided for each of the bending electromagnets 6–8, and each of the bending electromagnets 6–8 generates a magnetic field whose strength corresponds to the current fed to it. The respective value of the current outputted from the power sources 10 and 20 is determined by a control unit 30 based on the energy of the beam and other factors, and the determined values are set to the respective power sources by signals outputted from the control unit 30. Hereafter, a system composed of the bending electromagnet 6 to the bending electromagnet 8 is called a beam transport system.

In this embodiment, a scanning electromagnet 100 is provided between quadrupole electromagnets 3 and 4, and a scanning electromagnet 110 is provided in the irradiation nozzle 40 downstream of the bending electromagnet 8. The scanning electromagnet 100 is an electromagnet for deflecting the beam in a direction parallel to the deflection plane (X-Z plane shown in FIG. 1) created by the bending electromagnets 6, 7, and 8, and generates a magnetic field in the Y direction shown in FIG. 1, perpendicular to the deflection plane created by the bending electromagnets 6, 7, and 8. The scanning electromagnet 110 is an electromagnet for deflecting the beam in the Y direction shown in FIG. 1, perpendicular to the deflection plane creased by the bending electromagnets 6, 7, and 8, and generates a magnetic field in the direction parallel to the deflection plane. Power sources 150 and 160 are provided for feeding current to the scanning electromagnets 100 and 110, respectively, and a respective signal output from the control unit 30 is fed to each of the power source 150 and 160 to control the current applied to the scanning electromagnets 100 and 110, respectively. Thus, the scanning electromagnets 100 and 110 generate respective magnetic fields, corresponding to the quantities of fed current supplied thereto. By changing the strength of the magnetic fields generated by the scanning electromagnets 100 and 110 with time, by varying the respective output signals from the control unit 30 with time to change the quantities of the currents outputted from the power sources 150 and 160, it is possible to scan the diseased part with the beam. The values of the output signals sent from the control unit 30 to the power sources 150 and 160 are determined, teased on the shape of the diseased part, the intensity of the beam, and so forth.

Figure 2A:
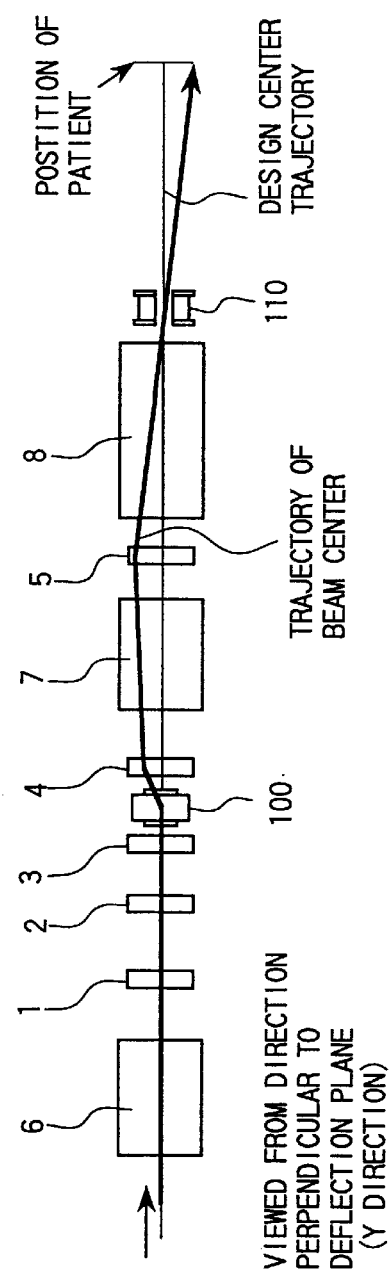
FIGS. 2A and 2B are schematic diagrams which show the center trajectory of the charged particle beam and the arrangement of electromagnets in the embodiment shown in FIG. 1.
Figure 2B:
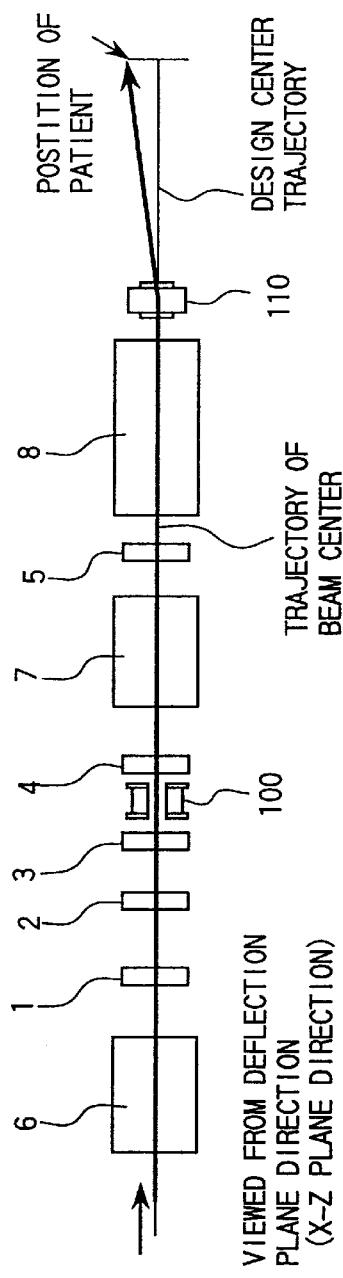

FIGS. 2A and 2B show the center trajectory of the charged particle beam and the arrangement of electromagnets in the embodiment shown in FIG. 1. Further, FIG. 2A is across sectional view of the rotation gantry viewed from the direction perpendicular to the deflection plane (X-Z plane) created by the bending electromagnets 6–8, and FIG. 2B is a cross sectional view of the rotation gantry viewed from the direction parallel to the deflection plane.

As shown in FIG. 2B, if the beam is viewed from the Y direction, the beam is deflected by the magnetic field generated by the scanning electromagnet 110, and the gradient of the center trajectory of the beam changes at the scanning electromagnet 110 in the Y direction. On the other hand, as shown in FIG. 2A, if the beam is viewed from the direction parallel to the X-Z plane, when the scanning electromagnet 100 generates the magnetic field in the direction perpendicular to the deflection plane created by the bending electromagnets 6–8, the gradient in the trajectory of the beam is changed, and the charged particle beam proceeds with a betatron oscillation downstream of the scanning electromagnet 100 by the action of the quadrupole electromagnets 4 and 5. That is, the beam deflected by the scanning electromagnet 100 is deflected toward the center direction of the rotation gantry by the quadrupole electromagnets 4 and 5, and passes the center of the scanning electromagnet 110. When the beam passes the scanning electromagnet 110, the difference between phases in betatron oscillation at the scanning electromagnets 100 and 110 is approximately 180 deg. Since the beam passes the center of the scanning electromagnet 110 as mentioned above, it is possible to narrow the gap between the magnetic poles of the scanning electromagnet 110, which can reduce the power consumption of the scanning electromagnet 110. The method of passing the beam through the center of the scanning electromagnet 110 will be explained later.

In the following, a method of controlling the scanning electromagnets 100 and 110 will be explained. The direction of scanning the diseased part of the patient with the beam is determined by the difference of phases in betatron oscillation in the scanning electromagnets 100 and 110. In this embodiment, since the difference of phases in betatron oscillation in the scanning electromagnets 100 and 110 is about 180 deg., the direction of scanning the diseased part with the beam at the scanning electromagnet 110 is reversed relative to the direction of deflection of the beam by the scanning electromagnet 100. Conversely, if the difference between the phases of betatron oscillation in the scanning electromagnets 100 and 110 is about 360 deg., the scanning direction of the beam in the diseased part is the same as that of the direction of deflection of the beam by the scanning electromagnet 100.

This control is performed based on the result of a computed analysis executed in advance or by using a beam position monitor 500. As mentioned above, if the difference between the phases of betatron oscillation in the scanning electromagnet and a beam scattering part is set to about 180 deg. or about an integer multiple of 180 deg., by adjusting the strength of the magnetic fields generated by the quadrupole electromagnets 4 and 5, as well as the bending electromagnets 7 and 8, the center of the beam can be made to coincide with the center of the scanning electromagnet 110 independently of the strength of the magnetic field in the scanning electromagnet 100.

Also, in this embodiment, two sine wave currents whose phases are shifted from each other by 90 deg. are fed to respective coils of the scanning electromagnets 100 and 110 from the power sources 150 and 160, and the amplitudes of the respective sine wave currents are adjusted so that, at the scanning electromagnet 110, the maximum gradient of the center trajectory of the beam in the X-z deflection plane is equal to that in the Y direction. Thus, the center of the charged particle beam moves circularly. Moreover, by feeding current of a saw tooth waveform or a chopped waveform to the scanning electromagnet 100, and by feeding a current whose quantity increases with the passage of time to the scanning electromagnet 110, it is possible to create a zigzag beam scanning pattern. Further, it is also possible to perform a control in which a current changing stepwise is fed to the respective scanning electromagnets 100 and 110, and the diseased part is irradiated by the beam only during the period when the change in time of the magnetic fields generated in the scanning electromagnets 100 and 110 is 0.

By using any one of the above-mentioned scanning methods, it is possible to create a narrow gap between the magnetic poles of the scanning electromagnet 110.

As seen in FIG. 1, downstream of the scanning electromagnet 110, a beam position monitor 500, a beam shape monitor 501 and a dose monitor 502 are provided, and the beam position, shape and dose are detected. The signals detected by the monitors are inputted into a data processing unit 50 and are converted to signals processable in the control unit 30. Further, the signals converted by the data processing unit 50 are inputted into the control unit 30. The control unit 30 controls the power sources 10, 20, 150, and 160, based on the respective detected signals. For example, the speed of scanning is controlled, based on the dose detected by the dose monitor 502.

Next, the method of passing the beam through the center of the scanning electromagnet 110 will be explained below. The following methods are applicable.

In a first method, if the arrangement of the quadrupole electromagnets and the bending electromagnets are determined in advance, after the position of the scanning electromagnet 110 is determined, the position of the scanning electromagnet 100 is set to a position upstream of the scanning electromagnet 110 so that the difference between phases in betatron oscillation of the beam in the two scanning electrodes is approximately 180 deg. Using this position setting of the scanning electromagnets 100 and 110, the beam passes the center of the scanning electromagnet 110. The position of the scanning electromagnet 100, at which the difference between phases in betatron oscillation of the beam in the two scanning electromagnets is approximately 180 deg., can be obtained by calculation.

In a second method, if the positions of the scanning electromagnets 100 and 110 are determined in advance, by adjusting the strength of the magnetic fields generated by one or more quadrupole electromagnets, it is possible to set the difference between phases in betatron oscillation of the beam in the two scanning electromagnets 100 and 110 to approximately 180 deg. The necessary strength of the magnetic fields generated by the quadrupole electromagnets can be obtained by calculation.

Although it is possible to obtain the positions of the scanning electrodes 100 and 110 and the necessary strength of the magnetic fields generated by the quadrupole electromagnets by calculation, the above positions and strengths can be adjusted, based on the results of detecting the beam position and the beam size, by using the beam position monitor 500 and the beam size monitor 500.

If the difference between phases in betatron oscillation at the scanning electromagnets 100 and 110 is about 180 deg., the beam passes the center of the scanning electromagnet 110 independently of the strength of the magnetic field generated in the scanning electromagnet 100.

That is, even if the trajectory of the beam center changes depending on the amount of deflection of the beam, which is performed by the scanning electromagnet 100, the beam always passes the center of the scanning electromagnet 110, and the beam crosses the design center trajectory of the beam at the center (the center trajectory of the charged particle beam when the beam is not deflected by any of the scanning electromagnets). Hereafter, the crossing point will be referred to as the focal point of the beam.

As mentioned above, by performing an adjustment to set the focal point of the beam at the center of the scanning electromagnet 110, it is possible to narrow the gap between the magnetic poles of the scanning electromagnet 110, which will lead to a reduction in the power consumption of the scanning electromagnet 110.

Figure 3:
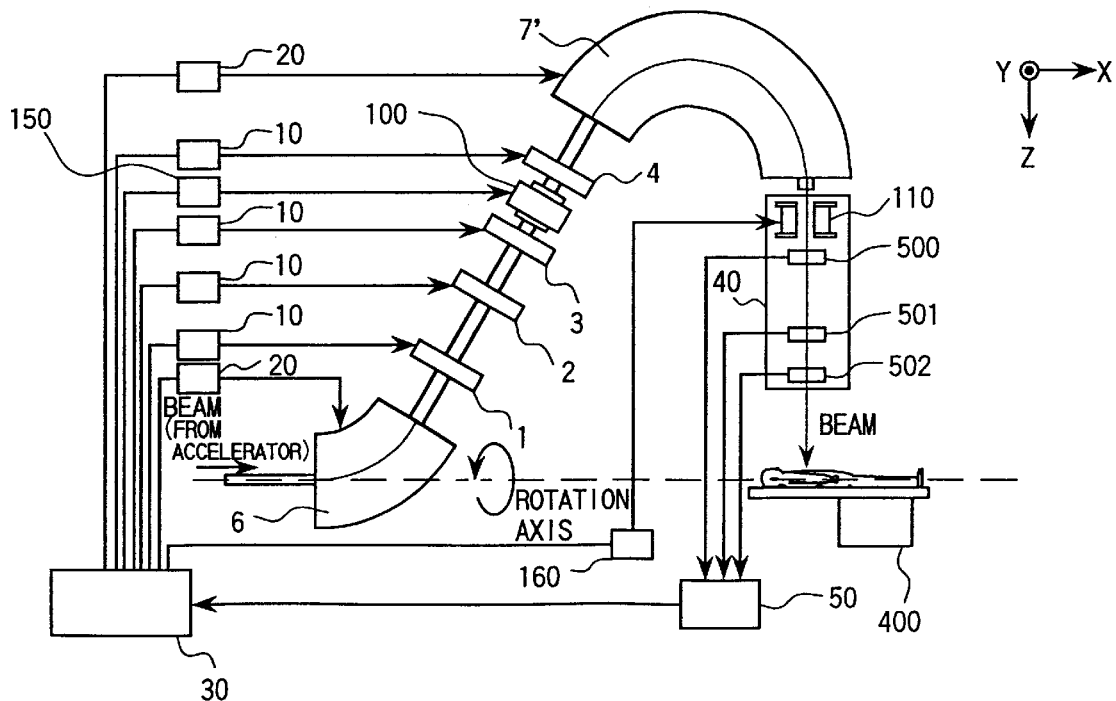
FIG. 3 is a schematic diagram showing the composition of a charged particle beam irradiation apparatus representing another embodiment of the present invention.

Embodiment 2:

A charged particle beam irradiation apparatus representing another embodiment of the present invention will be explained below with reference to FIG. 3. In the explanation of this embodiment, the features which are different from those of Embodiment 1 are mainly explained.

In this embodiment, the bending electromagnets included in a rotation gantry are composed of two electromagnets 6 and 7'. Since the number of bending electromagnets in the rotation gantry is less by one then that in Embodiment 1, it is possible to reduce the number of the power sources 20 controlled by the control unit 30 by one. Therefore, the control of the power sources performed by the control unit 30 becomes simpler, and the composition of the control unit 30 also can be simplified. Further, it is possible to obtain effects similar to those in Embodiment 1. Moreover, in this embodiment, the amount of deflection of the beam created by the quadrupole electromagnetic is adjusted so that the focal point of the beam is set at the center of the scanning electromagnet 110.

Embodiment 3:

A charged particle beam irradiation apparatus representing still another embodiment of the present invention will be explained below with reference to FIG. 4. In the explanation of this embodiment, the features which are different from those of Embodiment 1 are mainly explained.

Figure 4:
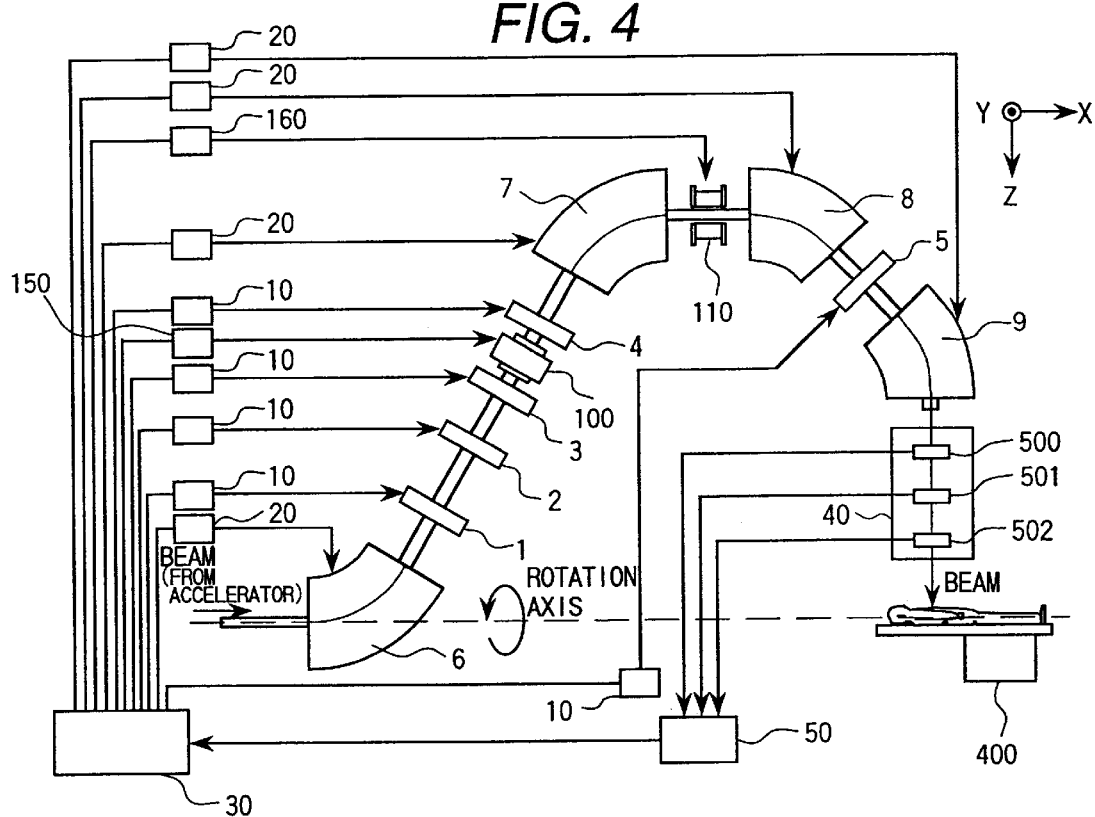
FIG. 4 is a schematic diagram showing the composition of a charged particle irradiation apparatus representing still another embodiment of the present invention.

In this embodiment, as shown in FIG. 4, the bending electromagnets included in a rotation gantry are composed of four electromagnets, and the scanning electromagnet 110 is placed between the bending electromagnets 7 and 8. Also, a bending electromagnet 9 is used, and the quadrupole electromagnet 5 is arranged downstream of the bending electromagnet 8.

FIGS. 5A and 5B show the center trajectory of the charged particle beam and the arrangement of the electromagnets in the embodiment shown in FIG. 4. FIG. 5A is a cross sectional view of the rotation gantry viewed from the direction perpendicular to the deflection plane (X-Z plane) created by the bending electromagnets 6–9, and FIG. 5B is a cross sectional view of the rotation gantry viewed from the direction parallel to the deflection plane.

As shown in FIG. 5A, if the beam is viewed from the direction parallel to the X-Z plane, the phase of the betatron oscillation of the beam deflected by the scanning electromagnet 100 is adjusted by the quadrupole electromagnet 4, and the focal point of the beam is set at the center of the scanning electromagnet 110. The beam which has passed the scanning electromagnet 110 passes the bending electromagnet 8, the quadrupole electromagnet 5, and the bending electromagnet 9, in turn. The beam is deflected by each of these electromagnets when the beam passes it, and the direction of the beam output from the bending electromagnet 9 is parallel to the design center trajectory of the beam. The necessary strength of the magnetic field to be generated in each of the quadrupole electromagnet 5, and the bending electromagnets 8 and 9 is determined in advance by calculation, and each of the power sources 10 and 20 are controlled, based on the calculated strength for each electromagnet.

By contrast, as shown in FIG. 5B, if the beam is viewed from the Y direction, the beam deflected by the scanning electromagnet 100 is deflected by each of the electromagnets when it passes the bending electromagnet 8, the quadrupole electromagnet 5 and the bending electromagnet 9, and the direction of the beam output 23 from the bending electromagnet 9 is parallel to the design center trajectory.

With embodiment, since the beam is outputted from the bending electromagnet 9 in a direction parallel to the design center trajectory of the beam, it is possible to reduce the dose to the normal cell structure surrounding the diseased area in comparison with an output beam which is inclined to the design center trajectory of the beam (fan beam). The effect of reducing the dose to the normal structure increases with the proximity to the body surface.

In addition, since the scanning electromagnet 110 is removed from the inside of the irradiation nozzle 40 to the beam transport system, the radius of rotation of the rotation gantry can be decreased. Therefore, the size of the building in which the rotation gantry is installed can be decreased, which can reduce the construction cost.

Also, in this embodiment, it is possible to obtain effects similar to those in Embodiment 1.

Furthermore, although the invention is not restricted to the composition shown in FIG. 4, if the following conditions are kept, that is, if the scanning electromagnet 110 is provided in the beam transport system of the rotation gantry, a bending electromagnet or a quadrupole electromagnet is placed downstream of the scanning electromagnet 110, and the rotation gantry is composed so that the focus of the beam is set at the center of the scanning electromagnet 110, it is possible to obtain effects similar to those in this embodiment.

Embodiment 4:

A charged particle beam irradiation apparatus representing yet another embodiment of the present invention will be explained below with reference to FIG. 6. In the explanation of this embodiment, the features which are different from those of Embodiment 1 are mainly explained.

Figure 6:
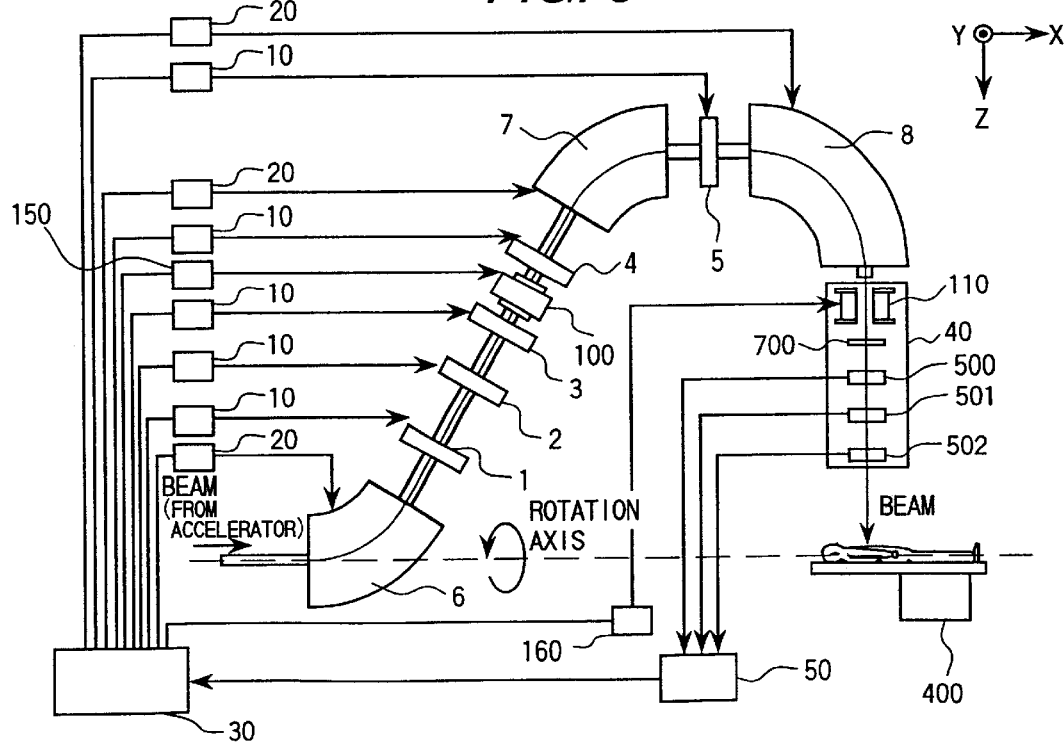
FIG. 6 is a schematic diagram showing the composition of a charged particle irradiation apparatus representing yet another embodiment of the present invention.
Figure 7:
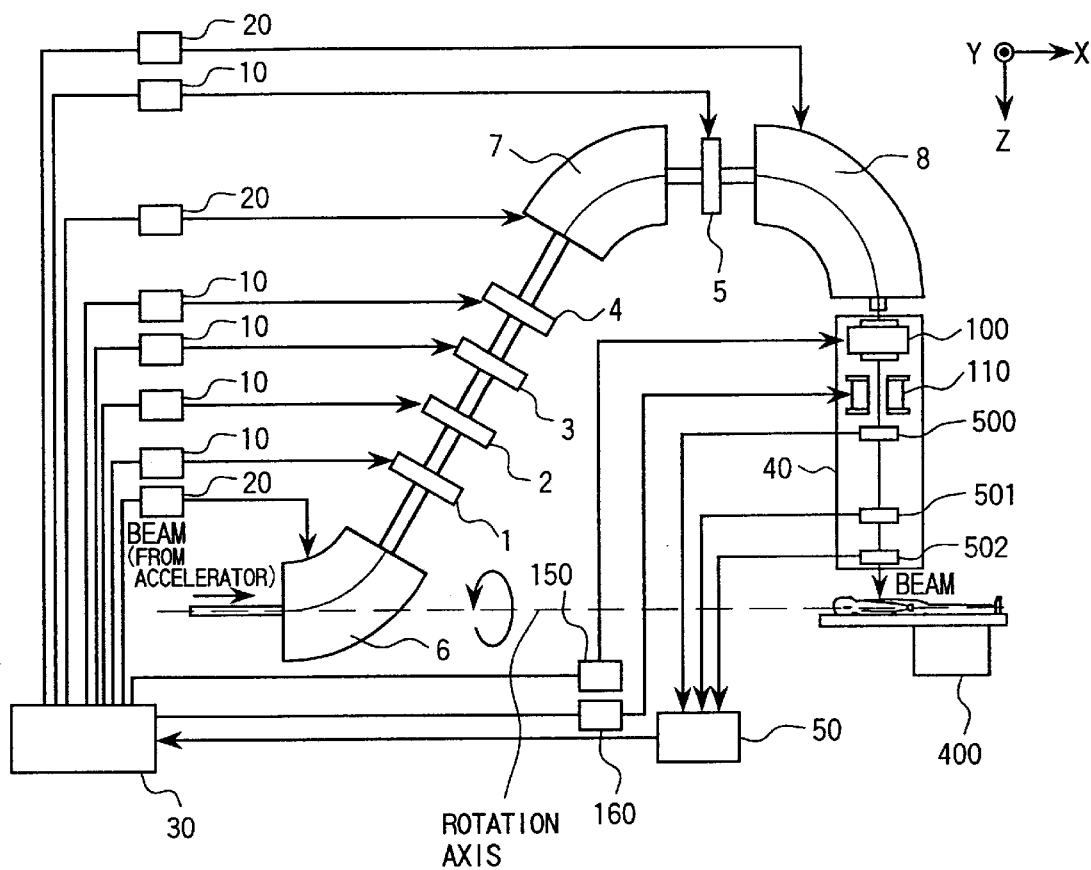
FIG. 7 is a diagram for explaining a conventional charged particle beam irradiation technique.

In this embodiment, as shown in FIG. 6, a beam scattering part 700 is used downstream of the scanning electromagnet 110. Therefore, the diameter of the beam output from the scanning electromagnet 110 is enlarged by the beam scattering part 700, and the diseased part is irradiated with a beam having an enlarged diameter. Thus, by enlarging the diameter of the beam using the beam scattering part 700, the extent of the scanning can be decreased, which can reduce the time for beam irradiation. In this embodiment, although the beam scattering part 700 is arranged downstream of the scanning electromagnetic 110, by providing the beam scattering part 700 at any place on the design center trajectory of the beam, it is possible to enlarge the diameter of the beam and to decrease the extent of the scanning operation. However, if the beam scattering part 700 is provided at a place in the upper stream of and far from the scanning electromagnet 110, since the gap between the magnetic poles of the scanning electromagnet 110 would need to formed wider, it is preferable to place the beam scattering part 700 downstream of the scanning electromagnet 110, or at a place downstream of and near the scanning electromagnet 110 (for example, between the scanning electromagnet 110 and the bending electromagnet 8).

Also, with this embodiment, by scanning with a beam controlled by the scanning electromagnets 100 and 110, and employing the effects of enlarging the diameter of the beam using the beam scattering part 700, a preset region can be uniformly irradiated.

Furthermore, even though the energy of the beam is changed, by using a beam scattering part 700, it is possible to keep the diameter of the beam constant. Since devices such as the beam position monitor 500, the beam shape monitor 501, the dose monitor 502, etc., are arranged in the irradiation nozzle 40, the beam is scattered by these devices, and its diameter is enlarged. If the energy of the beam is changed, the scattered state of the beam caused by these devices changes, and the diameter of the beam also changes. However, by exchanging the beam scattering part 700 automatically or by hand, the amount of change in the diameter of the beam can be corrected.

Also, in this embodiment, effects similar to those in Embodiment 1 can be obtained.

In the above-explained embodiments, although the focal point of the beam is set at the center of the scanning electromagnet 110, it is not always necessary to so set the focal point. If the focal point of the beam is set only within an effective magnetic field of the scanning electromagnet 110, the gap between the magnetic poles of the scanning electromagnet 110 can be narrowed sufficiently in comparison with that attained using conventional techniques. Moreover, in each embodiment, the difference between phases in betatron oscillation at the scanning electromagnets 100 and 110 is adjusted to 180 deg. However, if the difference is approximately an integer multiple of 180 deg., similar effects can be obtained.

Furthermore, in each embodiment, one or two quadrupole electromagnets are used downstream of the scanning electromagnet 100. However, even when more than two quadrupole electromagnets are provided, it is possible to obtain similar effects, if the distance between the scanning electromagnets 100 and 110 is such that the difference between phases in betatron oscillation in these scanning electromagnets is approximately 180 deg. or an integer multiple of 180 deg. Moreover, also concerning the relations among quadrupole electromagnets and bending electromagnets, if the distance between the scanning electromagnets 100 and 110 is such that the difference between phases in betatron oscillation at these scanning electromagnets is approximately 180 deg. or an integer multiple of 180 deg., the above relations is not restricted to those described in the embodiments.

In addition, in each embodiment, although electromagnets are used for deflecting the beam, it is possible to use permanent magnets which are rotated to generate a circular magnetic field used for performing circular scanning of a target. Furthermore, although a rotation gantry capable of rotating around a patient's bed is utilized in each embodiment described herein, by adequately arranging quadrupole electromagnets and bending electromagnets, the present invention is applicable to a stationary beam irradiation apparatus, a beam irradiation apparatus having a beam transport system of a linear composition, etc., and brings similar effects.

What is claimed is:

1. A charged particle beam irradiation apparatus comprising:
   a plurality of scanning electromagnets, for irradiating a target with a charged particle beam emitted from an accelerator;
   a quadrupole electromagnet;
   a power source for feeding current to said quadrupole electromagnet; and
   a control unit for controlling said current output from said power source;
   wherein two of said plurality of scanning electromagnets include a first scanning electromagnet, and a second scanning electromagnet located downstream of said first scanning electromagnet, and said quadrupole electromagnet which is located between said first and second scanning electromagnets enables adjustment of a phase of betatron oscillation of said charged particle beam, and wherein said control unit controls said current so that a difference between phases in the betatron oscillation of said charged particle beam in said first and second scanning electromagnets is approximately an integer multiple of 180 deg.

2. A charged particle beam irradiation apparatus of claims 1, further including at least one bending electromagnet and a power source for feeding current to said bending electromagnet, and a control unit for controlling said current fed from said power sources, wherein said control unit controls said current fed to said quadrupole electromagnet and said bending electromagnet so that a trajectory of the center of said charged particle beam is parallel to a design center trajectory of said beam irradiation apparatus at the position of said target.

3. A charged particle beam irradiation apparatus of claim 1, where at least one of another quadrupole electromagnet and a bending electromagnet is provided downstream of said second scanning electromagnet existing furthest downstream in said plurality of said scanning electromagnets.

4. A charged particle beam irradiation apparatus, including a plurality of scanning electromagnets, for irradiating a target with a charged particle beam emitted from an accelerator, wherein said plurality of said scanning electromagnets include a first scanning electromagnet and a second scanning electromagnet provided downstream of said first scanning electromagnet, and wherein a difference between phases in betatron oscillation of said charged particle beam in said first and second scanning electromagnets is approximately an integer multiple of 180 deg.

5. A charged particle beam irradiation apparatus of claim 4, wherein at least one of a quadrupole electromagnet and a bending electromagnet is provided downstream of said second scanning electromagnet existing furthest downstream in said plurality of said scanning electromagnets.

6. A charged particle beam irradiation apparatus of claim 4, further including at least one bending electromagnet and at least one quadrupole electromagnet, and power sources for feeding current to said quadrupole electromagnet and said bending electromagnet, and a control unit for controlling said current fed from said power sources, wherein said control unit controls said current fed to said quadrupole electromagnet and said bending electromagnet so that a said trajectory of the center of said charged particle beam is parallel to said design center trajectory of said beam irradiation apparatus at the position of said target.

7. A charged particle beam irradiation apparatus of claim 6, wherein said beam irradiation apparatus includes a rotation gantry, and said plurality of said scanning electromagnets are arranged in a beam transport system of said rotation gantry.

8. A charged particle beam irradiation apparatus of claim 7, a beam scattering part is provided on a trajectory of the charged particle beam.

9. A charged particle beam irradiation apparatus of claim 6, wherein a beam scattering part is used on said trajectory of said charged particle beam.

10. A charged particle beam irradiation apparatus of one of claims 1, 4, and 7, wherein said beam irradiation apparatus includes a rotation gantry, and said plurality of said scanning electromagnets are arranged in a beam transport system of said rotation gantry.

11. A charged particle beam irradiation apparatus of one of claims 1, 4, and 7, wherein a beam scattering part is provided in a trajectory of the center of said charged particle beam.

* * * * *